United States Patent [19]

De Bastiani et al.

[11] Patent Number: 5,019,077
[45] Date of Patent: May 28, 1991

[54] EXTERNAL SPLINT

[75] Inventors: Giovanni De Bastiani, Verona;
Giovanni Faccioli, Monzambano;
Roberto Aldegheri; Lodovico R.
Brivio, both of Verona, all of Italy

[73] Assignee: ORTHOFIX S.r.l., Bussolengo, Italy

[21] Appl. No.: 415,992

[22] Filed: Oct. 2, 1989

[30] Foreign Application Priority Data

Mar. 17, 1989 [IT] Italy ................ 84919 A/89

[51] Int. Cl.⁵ .................................... A61F 5/04
[52] U.S. Cl. .................... 606/54; 606/57; 606/59
[58] Field of Search ........... 606/53, 54, 59, 60, 606/61, 57; 403/53, 72, 79

[56] References Cited

U.S. PATENT DOCUMENTS

| | | | |
|---|---|---|---|
| 3,242,922 | 3/1966 | Thomas | 606/61 |
| 4,098,269 | 7/1978 | Judet | 606/73 |
| 4,308,863 | 1/1982 | Fischer | 606/57 |
| 4,604,997 | 8/1986 | De Bastiani et al. | 606/59 |
| 4,621,627 | 11/1986 | De Bastiani et al. | 606/57 |
| 4,714,076 | 12/1987 | Comte et al. | 606/59 |
| 4,745,913 | 5/1988 | Castaman et al. | 606/59 |

FOREIGN PATENT DOCUMENTS

3121271 12/1982 Fed. Rep. of Germany ... 128/92 ZZ

Primary Examiner—Robert A. Hafer
Assistant Examiner—Charles H. Sam
Attorney, Agent, or Firm—Ladas & Parry

[57] ABSTRACT

The present invention relates to an external splint which is particularly suitable for application to the pelvis, comprising a central body consisting of a plurality of members which can be connected together telescopically and do not rotate with respect to each other about their own axes, two screw holding clamps anchored with ball joints to the free ends of the central body and a removable contractor/extender device. An articulated member 22-23, 22-47-23 or 22-50-51-23 consisting of two or more parts can be inserted between parts 20, 21 of the central body allowing the said parts 20, 21 to rotate in a single plane containing the longitudinal axes of parts 20, 21 and at right angles to the plane passing through axes 25, 26 of the seats for the pins of the contractor/extender device. This rotation takes place around at least one of the pivot pins 24 which couples together the parts of the said articulated member.

15 Claims, 5 Drawing Sheets

EXTERNAL SPLINT

The invention relates to an external splint which is particularly suitable for application to the pelvis. This splint is a device for the external setting of broken bones or parts thereof of the type described in U.S. Pat. No. Re. 31,809. The splint mentioned in the said patent consists of a central body constructed of two parts which can move telescopically but cannot rotate with respect to each other, the ends of which are connected by means of ball joints to clamps holding bolts or screws.

Such split is provided with means for selectively immobilising the two parts of the central body at a desired length. It is also provided with a jack to extend or contract the length of the central body. This splint can be applied in order to solve problems associated with the large long bones, such as for example the tibia and femur.

Means of the type described in U.S. Pat. No. 4,621,627 are known for externally setting shorter bones such as the radius, ulna and the like, wherein the central body consists of at least three parts which can move telescopically with respect to each other, and the length of the central body can be extended in relation to its contracted length by means of a single device.

Both of these means described in the said patents have the characteristic that the parts forming the corresponding central bodies can be displaced only along the longitudinal axis of the splint itself, so that the centres of rotation of the ball joints which connect the bolt-holding clamps to the central body can also only lie along the said longitudinal axis. This characteristic, which is an advantage in some cases, in other cases illustrated below becomes an insuperable limitation to the correct use of the splint.

Splints of the type described above are also sometimes used in cases of diastasis of the pubic symphysis which may or my not be associated with subluxation or luxation of the sacroiliac joint, and in case of complex injury to the pelvis, such as for example fracture of the two arches or fracture and/or luxation of the sacroiliac.

Use of the said splints in these cases has proved to be very difficult and sometimes impossible, especially in cases where the patient suffers from some degree of obesity.

In such cases it is not possible to connect the screws attached to the iliac wings to the clamps of the splint because of the excessive abdominal volume which moves the central body of the splint away from the points to which the screws are fitted.

Sometimes the volume of the abdomen does not prevent the application of a known external splint, but it is sufficient to create serious difficulties for its correct application. In particular it is not possible to fix the screw-holding clamps at a short distance from the patient's skin.

Another disadvantage arises from the fact that it is sometimes necessary to provide a certain angle between the clamps of the splint which is greater than that provided by mere rotation of the clamps around the centres of the ball joints. This is found for example in cases of central luxation of the hip in which it is necessary to make a bridge connection to one iliac wing of the pelvis using the femur of the leg opposite the said iliac wing. In this case it is not possible to fit a known splint.

The object of the invention is to at least minimise the abovementioned disadvantages and in particular to provide a splint which is capable of taking up a wide range of positions and angular relationships with respect to the planes of the screws in the two screw-bearing clamps, while permitting rotation of the various parts of the splint, which always lie in a single plane containing the two centres of rotation of the ball joints of the screw-bearing clamps.

According to the present invention there is provided an external splint, particularly suitable for application to the pelvis, comprising a central body consisting of a plurality of members which can be inserted telescopically within each other but cannot rotate about their axes with respect to each other, two screw-holding clamps secured at the free ends of the central body by means of ball joints, a contractor/extender device which can be removably applied to the central body by inserting its pins into two seats provided in the central body, axial guide means between the parts of the central body which prevent rotation and allow selective immobilisation and means to immobilise the screw-holding clamps in a stable position with respect to the central body, in which an articulated member can be inserted between the two parts of the central body allowing the said parts to rotate in a single plane obtaining the longitudinal axes of the parts and at right angles to the plane passing through the axes of the seats housing the pins of the contractor/extender device, the said rotation taking place around at least one of the axes of the pivot pins which couple together the parts of the said articulated member.

The main advantage offered by the proposed arrangement lies in the fact that a device according to the invention solves a number of orthopaedic problems where in the past the surgeon had of necessity to make use of techniques other than external splinting.

In particular external splints may be used in the abovementioned cases of fracture of the pelvis or to immobilise parts of the pelvis, especially in obese patients.

Another advantage is provided by the fact that by displacing the central parts the splint according to the invention, the splint can easily be transformed into an external axial splint, that is one in which the centres of rotation of the ball joints for the clamps always lie on the longitudinal axis of the splint, so that a wide range of orthopaedic situations can be covered with a single device.

A further advantage is provided by the fact that some axial external splints already available commercially of the type described in the abovementioned United States patents may be converted into external splints for the pelvis through the insertion of an articulated member according to the invention between two members of the central body of the original splint.

This obviously provides a double saving in that the parts which are common to axial splints and pelvic splints can be manufactured in a standardised way, and also the possessors of external axial splints compatible with the object of the invention may extend the range of use of the old splints merely by acquiring the central portions comprising the articulated member whereby the range of possible angular relationships between the screw-bearing clamps may be increased.

It should also be noted that not only in the case of obese patients does use of the splints according to the invention make it possible for the splint itself to be more correctly positioned, i.e. with the screw-holding clamps in a position as close as possible to the patient's skin, compatible with the minimum distance necessary for treating the wounds caused by insertion of the said screws. This prevents the formation of abnormal dangerous stresses in the screws which might cause movement of a screw in the bone, or even fracture of the bone at the point where the stressed screw is inserted.

The present invention will be further illustrated, by way of example, with reference to the accompanying drawings, in which.

Figure 1:
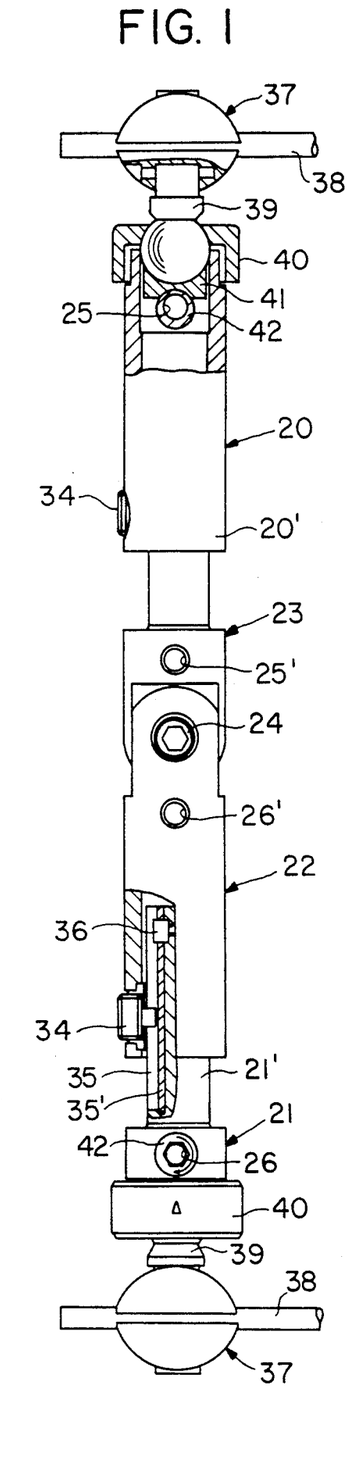
FIG. 1 is a side view in partial cross-section of a pelvic splint according to the invention.
Figure 2:
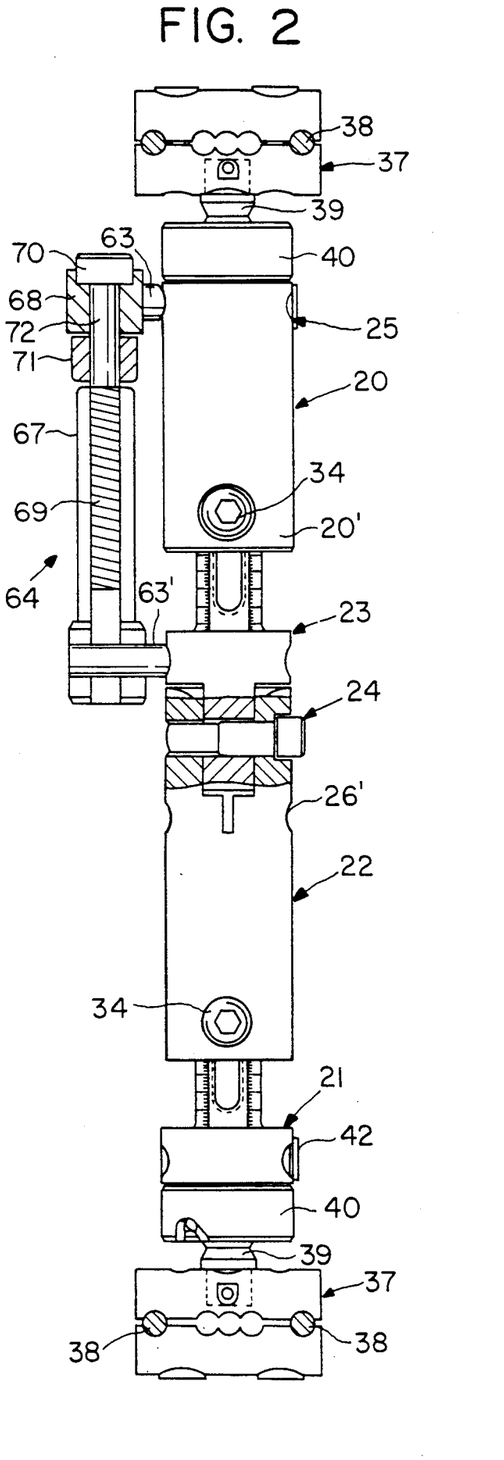
FIG. 2 is a side view similar to that of FIG. 1, but with the device rotated through 90° and also including a partial cross-sectional view of the contractor/extender device. For the sake of clarity, the contractor/extender device is not illustrated in the other Figures.

Bearing in mind that in the figures the same numerals indicate identical or equivalent parts, with reference to FIGS. 1 and 2 it will be noted that the splint according to the invention comprises a central body consisting of four parts 20, 23, 22, 21, two T-shaped clamps 37, bearing screws 38 which are anchored to the free ends of the central body by means of ball joints 39, selectively operable axial anti-rotation and securing guide means 34, 35' between the parts of the central body and means 40, 41, 42 to immobilise the screw-holding clamps in a stable position with respect to the ends of the central body of the splint.

The splint is completed, by a contractor/extender device of the type described in U.S. Pat. No. Re. 31,809 mentioned previously, which can be fitted to the central body in a removable way by inserting its two pins into one of the two pairs of seats 25, 25' and 26, 26' provided in the sides of the central body. The contractor/extender device 64 includes a hollow cylinder 67 to which the pin 63' is secured at the lower end thereof, a second hollow cylinder 68 to which the pin 63 is secured, a screw 69, the head 70 of which is mounted in the hollow cylinder 68 and a collar or sleeve 71 which is securely connected to a rod section 72 of the screw 69, the outer thread of which engages in the internal thread of hollow cylinder 67. As soon as the pins 63, 63' have been inserted into the seats 25 and 25' or 26 and 26', located respectively in the elongated members 20 and 23 or 20 and 21, it suffices to screw in the screw 69 by actuating the head 70, in order, as required, to cause a mutual approach or separation of the elongated members 20 and 23 or 21 and 22 of the central body.

The parts forming the central body are at the upper end a part 20 and at the lower end a part 21, and in a central position with respect to the said parts 20 and 21, a male part 23 above and a female part 22 below.

Part 20 consists of a hollow cylindroid having an almost elliptical transverse cross-section with a through cylindrical internal cavity having at its upper end a seat housing means 40, 41, 42 for immobilising ball joint 39 which attaches a clamp 37 bearing screws or bolts to said part 20 of the central body. These means are illustrated in particular in U.S. Pat. No. 4,621,627 mentioned previously. In these means the eccentric tubular plug 42 forms the seat 25 for one of the two pins of the contractor/extender device.

Part 20 bears on its other end means 34, 43 which axially guide, prevent the rotation of and selectively immobilise part 20 with respect to the other part of the central body to which it is connected. The said means consist of a threaded hole 43 having its longitudinal axis at right angles to the longitudinal axis of part 20 itself, and a securing screw 34 which can be screwed into the said hole and has an allen head and which projects by means of its end 45 into the longitudinal cylindrical cavity of part 20. These means act together with corresponding means 35, 35', 36 provided on the other part of the central body to which it is connected, illustrated earlier, and have the function of preventing part 20 from rotating about its own longitudinal axis with respect to the other part of the central body and of allowing relative axial movement between the parts connected when screw 34 is slackened.

Part 21 at the other end of the central body consists of a substantially cylindrical shaft of a diameter such that it can be inserted into the longitudinal cylindrical cavity of part 20. This shaft has a head with an external configuration corresponding to the cylindroid of part 20 in which is provided seat 26 for housing one of the two pins of the contractor/extender device. Said part 21 also has at its lower end means 40, 41, 42 for immobilising ball joint 39 of the second screw-holding clamp 37. This shaft is also provided with means 35, 35', 36 for guiding, preventing the rotation of and selectively immobilising part 21 itself with respect to the other part of the central body to which it is attached, which in the case of FIG. 1 is part 22, illustrated subsequently.

Figure 6:
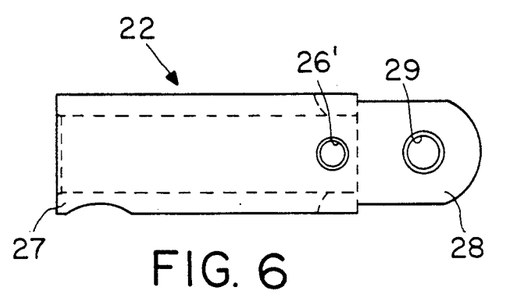
FIG. 6 is a side view of the female part of the articulated member of the splint of FIG. 1.
Figure 7:
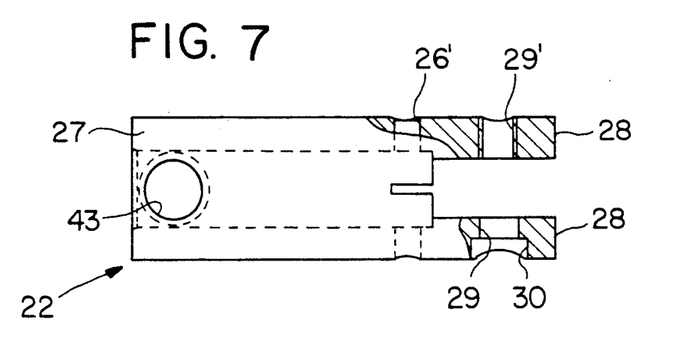
FIG. 7 is a view from above of the female part of the articulated member of FIG. 6.
Figure 8:
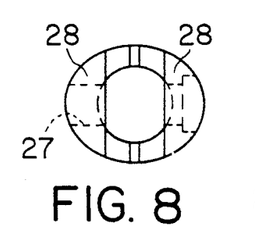
FIG. 8 is a frontal view of the female part of the articulated member of FIG. 6.

Female part 22 illustrated in detail in FIGS. 6, 7 and 8 has one end 27 which reproduces the precise outline of the free end 20' of part 20 of the central body of the splint, provided with corresponding axial guide means which prevent rotation and permit selective immobilisation 34, 43, while the other end 28 of said part 22 consists of the female member of a pivot joint. This part is provided with two grooves 46 parallel to the longitudinal axis of the said part and placed in accordance with the plane of symmetry of the two arms of the female member of the pivot joint, the said grooves having the function of making the two arms of the pivot flexible in such a way that the two arms can be brought together elastically with greater ease when pin 24 of the pivot which is screwed into its own seat 29, 30 compresses the said arms against the male member of the joint to immobilise the said joint in a given position.

Figure 3:
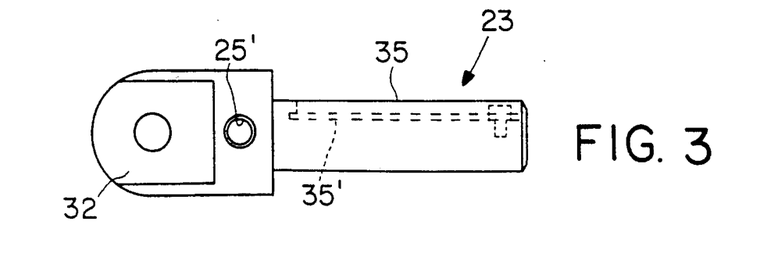
FIG. 3 is a side view of the male part of the articulated member of the splint of FIG. 1.
Figure 4:
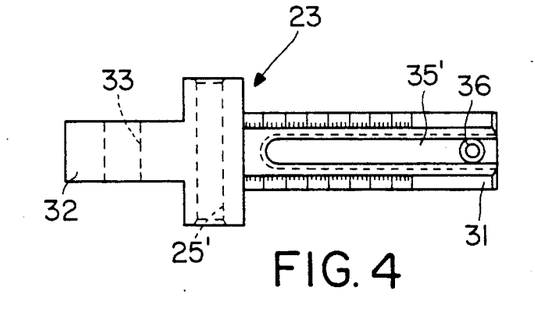
FIG. 4 is a view from above of the male part of the articulated member of FIG. 3.
Figure 5:
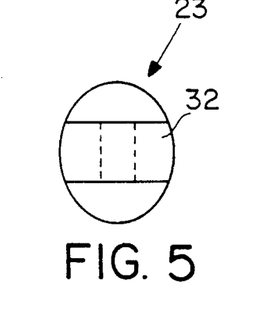
FIG. 5 is a frontal view of the male part of the articulated member of FIG. 3.

Male part 23, which is illustrated in detail in FIGS. 3, 4 and 5, has one end 31 which reproduces the precise outline of free end 21' of part 21 of the central body of the splint, with corresponding means for axial guidance, prevention of rotation and selective immobilisation 35, 35', 36, consisting of groove 35 made in the base of a metal sheet 35' and a securing dowel 36 which acts together with the said means 34, 43 provided on part 22. The other extremity 32 of said part 23 consists of the male member of a pivot joint.

Figure 9:
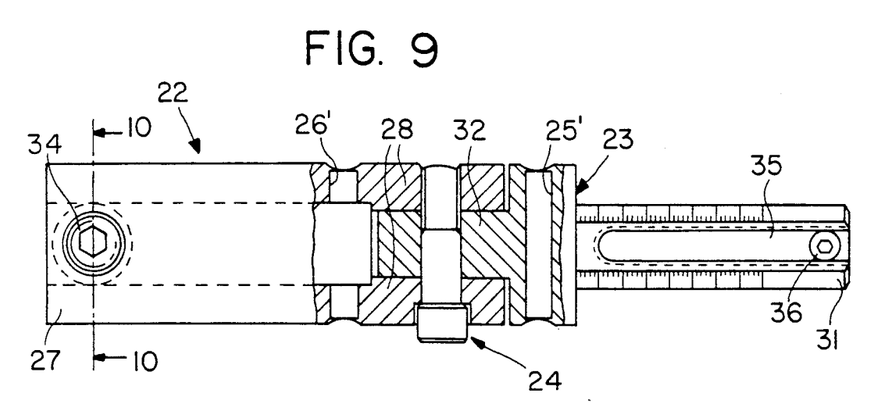
FIG. 9 is a view from above in partial cross-section of a first embodiment of the articulated member of splint according to the invention, which is in two parts.
Figure 10:
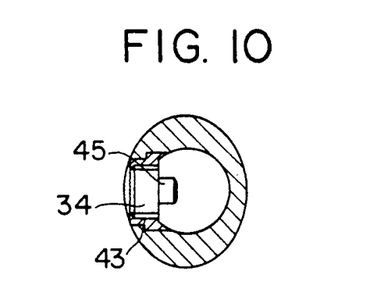
FIG. 10 is a sectional view along the line 10—10 of FIG. 9.
Figure 11:
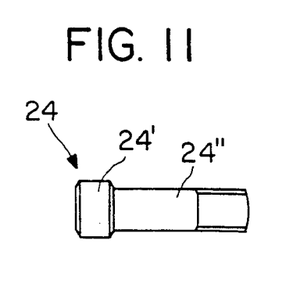
FIG. 11 is a side view of a particular embodiment of the pivot pin.
Figure 12:
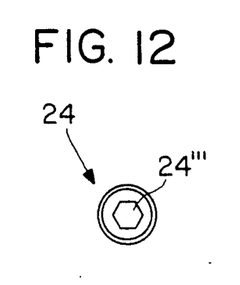
FIG. 12 is a frontal view of the pin of FIG. 9.

Said parts 22 and 23 which are joined together by a pivot joint constitute a particular and distinctive element of the invention, also described as the articulated body, illustrated as a whole in FIG. 9. The two male and female members of the said joint are held together by a pin 24, illustrated in FIGS. 11 and 12, which has a cylindrical head 24' with a recessed hexagon 24''', the partially threaded shank 24'' of which is screwed into threaded hole 29' made in one of the two arms of the female member of the fork.

The principal characteristics of the said articulated body consist of the fact that it can be inserted telescopically between the two parts 20, 21 of the central body of an axial splint.

Following such insertion the relative movements between parts 20 and 21, which in axial splints consist only of axial displacement between the two parts, are amplified by the addition of relative rotation of the two parts around an axis at right angles to their longitudinal axis. This rotation takes place in a single defined plane which contains the longitudinal axes of parts 20, 21 themselves and is at right angles to the plane passing through the axes of seats 25, 25' and 26, 26' in which the pins of the contractor/extender device are held. This rotation obviously takes place about the axis of pin 24 of the pivot.

In this way the range of the angular relationship in the said plane between the planes of the screws inserted into the clamps is appreciably widened when compared with that of known axial splints.

In fact in such splints this angular relationship depends exclusively on rotation of the clamps about the centres of rotation of their ball joints, and is therefore extremely limited.

Introduction of the articulated body between the two parts of a central body of an axial splint makes it possible to have two pairs of seats 25, 25' and 26, 26' to house the pins of the contractor/extender device. In this way the orthopaedic surgeon can operate the said device in two different positions, depending on whether it is desirable to operate with compression or tension in the proximity of one or other of the screw-holding clamps.

Figure 13:
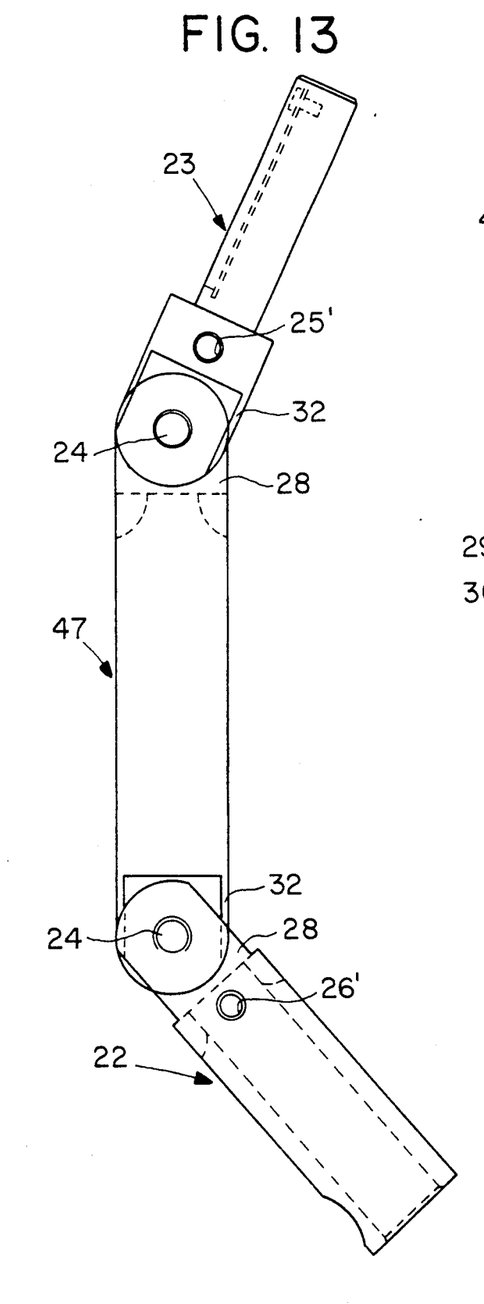
FIG. 13 is a side view of a second embodiment of an articulated member constructed in three parts.

FIG. 13 illustrates a second embodiment of the articulated body which consists of three parts 22, 47 and 23.

In comparison with the embodiment already illustrated, this embodiment allows the splint to adopt a wider range of positions and angular relationships between the planes of the screws in the two screw-holding clamps. In particular this is very useful in cases of central luxation of the hip, where it is necessary to connect the iliac wing with the opposite femur in order to provide traction between the parts with an orientation parallel to the axis of the neck of the femur.

This embodiment differs from the foregoing through the introduction of a third part 47 between the two parts 22 and 23 of the articulated body already illustrated, this third part consisting of a cylindroid of almost elliptical solid cross-section which is externally identical to that of the other parts 20, 21, 22 and 23 of the splint.

Figure 14:
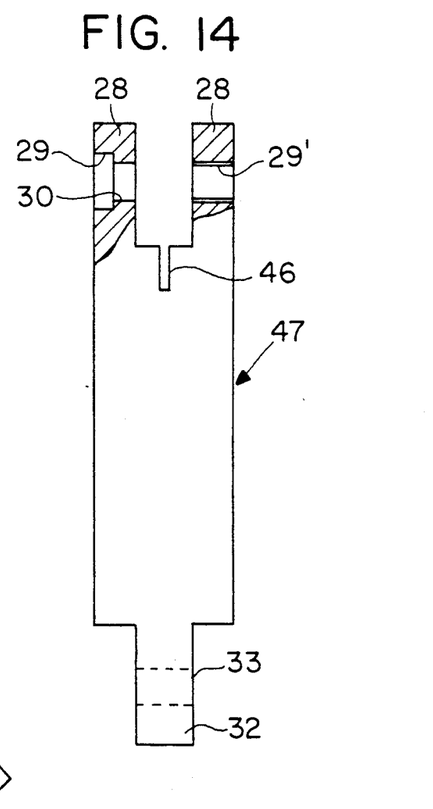
FIG. 14 is a view in partial cross-section of the central part of the articulated member illustrated in FIG. 13, but rotated through 90°.
Figure 15:
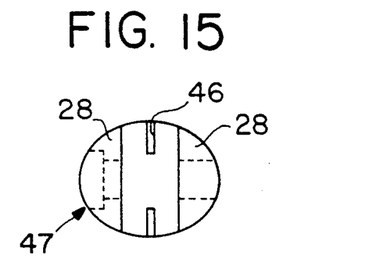
FIG. 15 is a frontal view of the central part of the articulated member illustrated in FIG. 14.

The ends of said part 47, illustrated in detail in FIGS. 14 and 15, reproduce respectively the female member 28 and the male member 32 of the pivot joint which connects parts 22 and 23 previously described.

In this way a two part articulated body 22 and 23 may be converted into a three part articulated body connected by two pivot joints. All that is necessary in fact is to dismantle the two part articulated member by removing pin 24 from the pivot and attaching first the female extremity of part 47 to the male extremity 32 of part 23 with a pin 24 and then the other male extremity of said part 47 to the female extremity 28 of part 22 with a second pin 24.

Figures 16, 17:
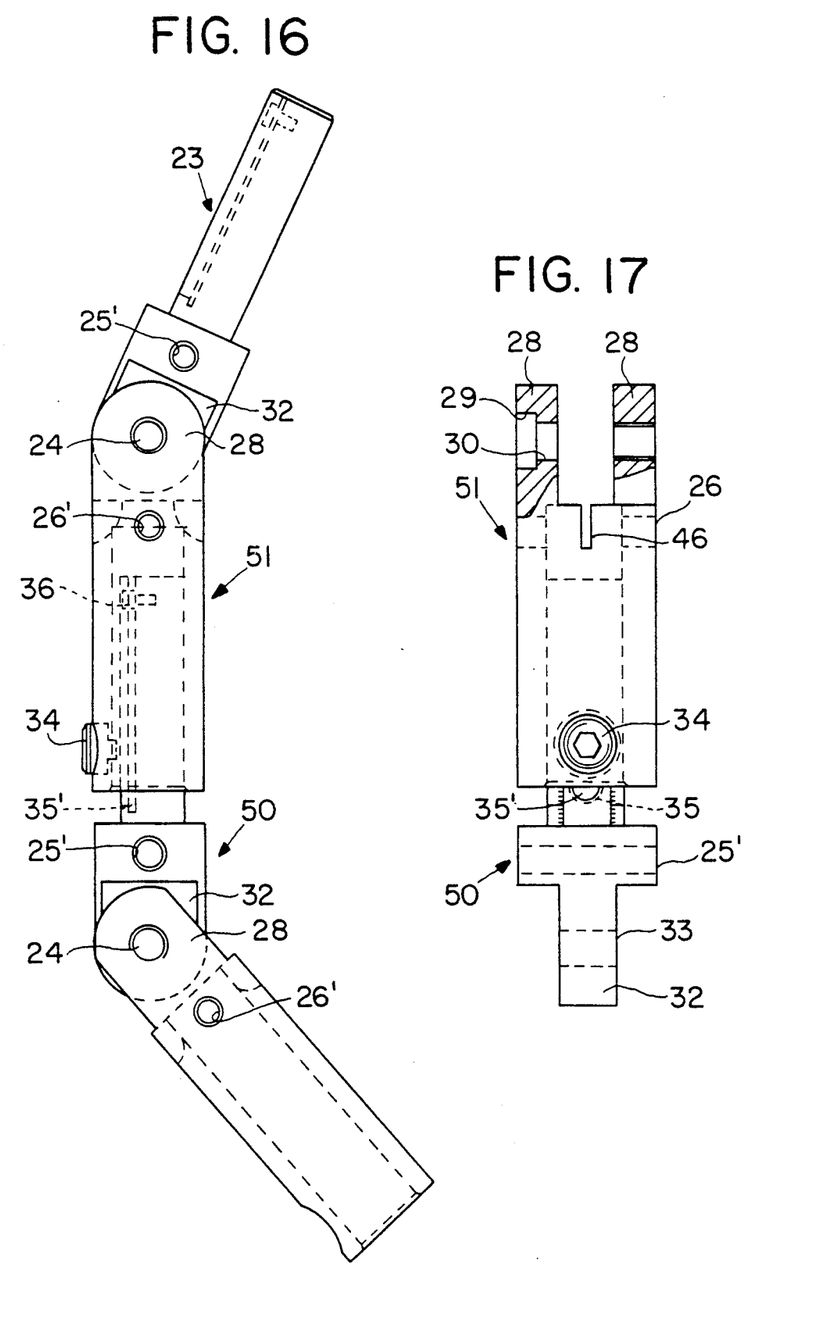
FIG. 16 is a side view of a third embodiment of an articulated member in three parts in which the central part itself consists of two parts.
FIG. 17 is a view in partial cross-section of the central parts of the articulated member illustrated in FIG. 16, but rotated through 90°.

FIG. 16 illustrates a third embodiment of the articulated body which again consists of three parts 22, 50-51 and 23, but in which the third central part now in turn consists of two parts, a male part 50 and a female part 51 which can move telescopically with respect to each other. Said parts 50 and 51 are also provided with rotation-preventing axial guide means 34, 35-35', 36 similar to those already described and applied to the free ends of parts 20 and 21 of the splint. The said parts 50 and 51 are respectively of a shape which is substantially identical to male 23 and female 22 parts of the said articulated member, and which may only differ from the latter in their corresponding length.

The three parts 20, 50-51, 23 are therefore joined together by means of two pivot joints with pins 24 which have their own longitudinal axes strictly parallel to each other, but can nevertheless be displaced with respect to each other along the longitudinal axis of part 50-51. This displacement of the axes of pins 24 takes place by sliding the shaft of part 50 into part 51 while rotation-preventing axial guide means 34, 35-35', 36 prevent parts 50 and 51 from rotating about their own axis. In comparison with the embodiment already illustrated, this embodiment allows the splint to achieve an even greater range of positions and angular relationships between the planes of the screws of the bolt-holding clamps and is particularly useful when connecting the iliac wing to the opposite femur in the case of central luxation of the hip, and in particularly obese patients.

It is clear that the articulated member which can be removably inserted between parts 20 and 21 of an axial splint may also consist of central parts connected together by means of pivot joints where the axes of the pins are all parallel to each other.

Also the said central parts may be either of the type consisting of a single piece or of the type consisting of two parts which can move telescopically with respect to each other.

Even though not illustrated in the drawings, it is clear that the position of the male member and the female member of the pivot joint may be exchanged with respect to parts 22 and 23, i.e. the male member may be placed on part 22 and the female member on part 23.

Even though it is not shown in the drawings, it is clear that at least one of the T-clamps may be replaced by a standard clamp so as to have the axis of the screws in a plane passing through the centre of rotation of the ball joint of the said clamp.

We claim:

1. An external splint, particularly suitable for application to the pelvis, comprising:
   first and second screw-holding clamps; and
   a central body connected between said screw-holding clamps, said central body comprising first, second, third and fourth elongated members and first and second ball joints coupling said central body to said first and second clamps, respectively; and wherein:
   said first elongated member has one end portion coupled to said first ball joint and a second end portion telescopically engaging a corresponding first end portion of said second elongated member;
   said second elongated member has a second end portion which forms a first part of a pivot joint;
   said third elongated member has one end portion forming a second part of the pivot joint, said two parts of the pivot joint being pivotally journalled to allow movement of said second and third elongated members in a single plane;
   said third elongated member has a second end portion adapted to telescopically engage with a first end portion of a fourth elongated member;
   said fourth elongated member has a second end portion coupled to said second ball joint;
   each of said telescopically engaging end portions have axial guide and locking means for preventing rotation and to selectively immobilize said telescopically engaging members;
   said ball joints include means for immobilizing the ball joints of the screw-holding clamps relative to said central body; and said first and second parts of said pivot joint includes means for immobilizing said first and second parts of said pivot joint.

2. An external splint as claimed in claim 1, wherein:
   said central body further comprises a pivot pin having a head and a shaft;
   the second end portions of the first and third telescopically engagable elongated members are female end portions, and the first end portions of said second and fourth elongated members are male end portions;
   the first part of the pivot joint is a male portion having a flat planar blade with a hole defined therethrough, said hole having an axis perpendicular to the flat blade, said flat planar blade being parallel to a longitudinal axis of the second elongated member;
   the second part of the pivot joint is a female portion having two arms having opposite facing parallel flats, said parallel flats each having a hole defined therethrough, each said hole having an axis perpendicular to the flats of the two arms, the hole in one of the arms being enlarged to form a seat for the head of the pivot pin, the hole in the other arm being sized to receive the shaft of the pivot pin;
   such that when said flat planar blade of the male portion of the pivot joint is inserted between the two arms of said female portion of the pivot joint, the holes in the two parts line up and the pivot pin can be inserted therethrough, and alternately loosened or tightened to selectively immobilize the second and third elongated members with respect to each other in a desired orientation in said single plane.

3. An external splint as claimed in claim 2, further comprising a contractor/extender device connected to one pair of said telescopically engagable elongated members, and wherein:
   said contractor/extender device has two pins extending laterally therefrom;
   each of said telescopically engagable elongated members connected to said contractor/extender has a seat for receiving one of said pins so as to permit lengthening or shortening of the telescopically cooperating elongated members to which the contractor/extender device is affixed.

4. An external splint as claimed in claim 2, wherein said pivot pin has an allen head and a shaft being at least partially threaded at its end, and wherein said hole in said arm of said female portion sized to receive the shaft of the pivot pin is threaded, such that the pivot pin can be alternately loosened or tightened to selectively immobilize the second and third elongated members with respect to each other in a desired orientation in said single plane.

5. An external splint as claimed in claim 2, further comprising:
   a second pivot pin having a head and a shaft; and
   a fifth elongated member placed between said second and third elongated members, said fifth elongated member having first and second end portions;
   wherein said first portion of the fifth elongated member is similar to said female end portion of the pivot joint of the third elongated member and the second portion of the fifth elongated member is similar to said male portion of the pivot joint of the second elongated member, thereby forming two pivot joints, one at each end of said fifth member, said first and second pivot pins being received in the holes defined in the pivot joints, wherein the axes of the holes defined in the pivot joints of the fifth elongated member are parallel.

6. An external splint as claimed in claim 2, further comprising a second pivot pin having a head and a shaft; and
   fifth and sixth telescopically engagable members, each of said fifth and sixth telescopically engagable members having first and second end portions, said first end portion of said fifth elongated member being similar to the female portion of the pivot joint of the third elongated member, said second end portion of said fifth elongated member being a female end portion, said first end portion of said sixth elongated member being a male portion, and said second end portion of the sixth elongated member being similar to said second end portion of the second elongated member, wherein said first and second pivot pins are received in the holes defined in the first and second pivot joints respectively, wherein the axes of the holes defined in the pivot joints of the fifth and sixth elongated members are parallel, and wherein the telescopically engagable fifth and sixth elongated members are provided with axial guide and locking means for preventing rotation and to selectively immobilize said telescopically engaging members.

7. An external splint as claimed in claim 2, wherein said allen head of said pivot pin is an allen head and protrudes beyond the outer perimeter of the first and third elongated members.

8. An external splint as claimed in claim 2, wherein said shaft of said pivot pin is wholly smooth and unthreaded on its outside surface but is internally threaded at its end opposite the head which is an allen head, and wherein a threaded pin is inserting and tightened into the threaded hole of said pivot pin after said pivot pin is inserted into the holes in the pivot joints, and thereby cause said female arms of said pivot joint to clamp around the male portion of the pivot joint.

9. An external splint as claimed in claim 2, wherein said pivot pin has an allen head and a shaft being at least partially threaded at its end and said hole in said arm of said female portion sized to receive the shaft of the pivot pin being threaded, such that the pivot pin can be alternately loosened or tightened to selectively immobilize the second and third elongated members with respect to each other in a desired orientation.

10. An axial splint as claimed in claim 4, wherein said heads of said pivot pins are allen heads and protrude beyond the outer perimeter of the third and fourth elongated members.

11. An external splint as claimed in claim 4, wherein said shafts of said pivot pins are wholly smooth and unthreaded on their outside surfaces but are internally threaded at their ends opposite the heads which are allen heads, and wherein a threaded pin is inserting and tightened into the threaded hole of said pivot pins after said pivot pins are inserted into the holes in the pivot joints, and thereby cause the female arms of the pivot joints to clamp around the male portions of the pivot joints.

12. An external splint as claimed in claim 4, wherein said pivot pins have allen heads and a shaft being at least partially threaded at their ends opposite the allen heads, and said holes in said arms of said female portions sized to receive the shafts of the pivot pins being threaded, such that the pivot pins can be alternately loosened or tightened to selectively immobilize the second and fifth and fifth and third elongated members with respect to each other in a desired orientation.

13. An axial splint as claimed in claim 5, wherein said heads of said pivot pins protrude beyond the outer perimeter of the outer perimeter of the third and fifth elongated members.

14. An external splint as claimed in claim 5, wherein said shafts of said pivot pins are wholly smooth and unthreaded on their outside surfaces but are internally threaded at their ends opposite the heads which are allen heads, and wherein a threaded pin is inserting and tightened into the threaded hole of said pivot pins after said pivot pins are inserted into the holes in the pivot joints, and thereby cause the female arms of the pivot joints to clamp around the male portions of the pivot joints.

15. An external splint as claimed in claim 5, wherein said pivot pins have allen heads and a shaft being at least partially threaded at their ends opposite the allen heads, and said holes in said arms of said female portions sized to receive the shafts of the pivot pins being threaded, such that the pivot pins can be alternately loosened or tightened to selectively immobilize the second and fifth and sixth and third elongated members with respect to each other in a desired orientation.

* * * * *